United States Patent [19] [11] 4,375,964
Knopp et al. [45] Mar. 8, 1983

[54] DENTAL INSTRUMENT HAVING A LAMP ASSEMBLY SUSPENSION INCLUDING VIBRATION AND THERMAL ISOLATION MEANS

[75] Inventors: Arthur A. Knopp, Chalfont; Leonard J. Kelly, Norristown, both of Pa.

[73] Assignee: Syntex (U.S.A.) Inc., Palo Alto, Calif.

[21] Appl. No.: 203,188

[22] Filed: Nov. 3, 1980

Related U.S. Application Data

[63] Continuation of Ser. No. 12,630, Feb. 16, 1979, abandoned.

[51] Int. Cl.³ .............................................. A61C 1/00
[52] U.S. Cl. ...................................................... 433/29
[58] Field of Search ........................................ 433/29

[56] References Cited

U.S. PATENT DOCUMENTS

| 2,539,828 | 1/1951 | Goldes et al. | 433/29 |
| 3,295,514 | 11/1967 | Hein et al. | 433/32 |
| 3,614,414 | 10/1971 | Gore | 433/29 |
| 3,634,938 | 1/1972 | Hutchinson | 433/29 |

FOREIGN PATENT DOCUMENTS

| 1412622 | 12/1972 | United Kingdom | 433/29 |
| 1362135 | 9/1974 | United Kingdom | 433/29 |

Primary Examiner—Robert Peshock
Attorney, Agent, or Firm—John A. Dhuey; Joseph I. Hirsch

[57] ABSTRACT

A dental instrument is disclosed having a light source assembly suspension which includes resilient means, such as a coil spring, for supporting the lamp assembly while at the same time reducing vibration that may be transmitted from the instrument to the light source assembly. The resilient means also reduces heat loss from the light source assembly to the dental instrument so that shorter filament warm-up time is provided. The light source assembly suspension is particularly useful in a dental handpiece in which the frequency of vibration of the gas-driven motor may coincide with one of the harmonic frequencies of vibration of the lamp filament or filament support.

37 Claims, 7 Drawing Figures

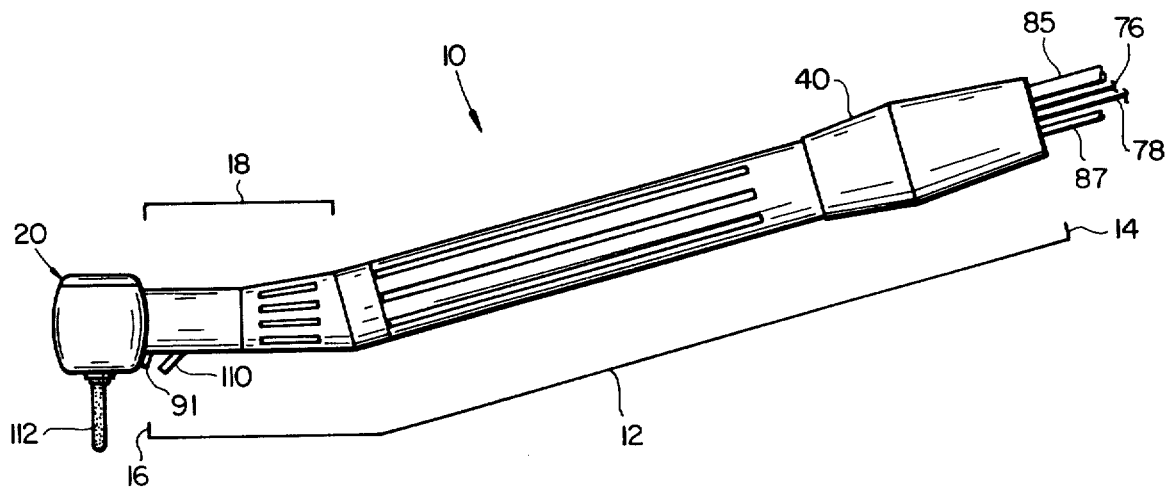
FIG_1
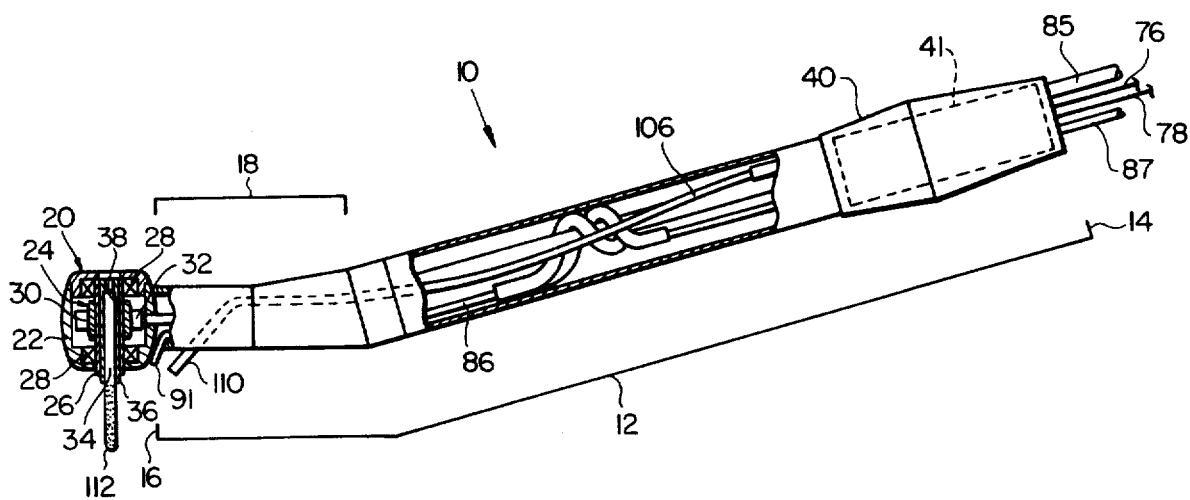
FIG_2

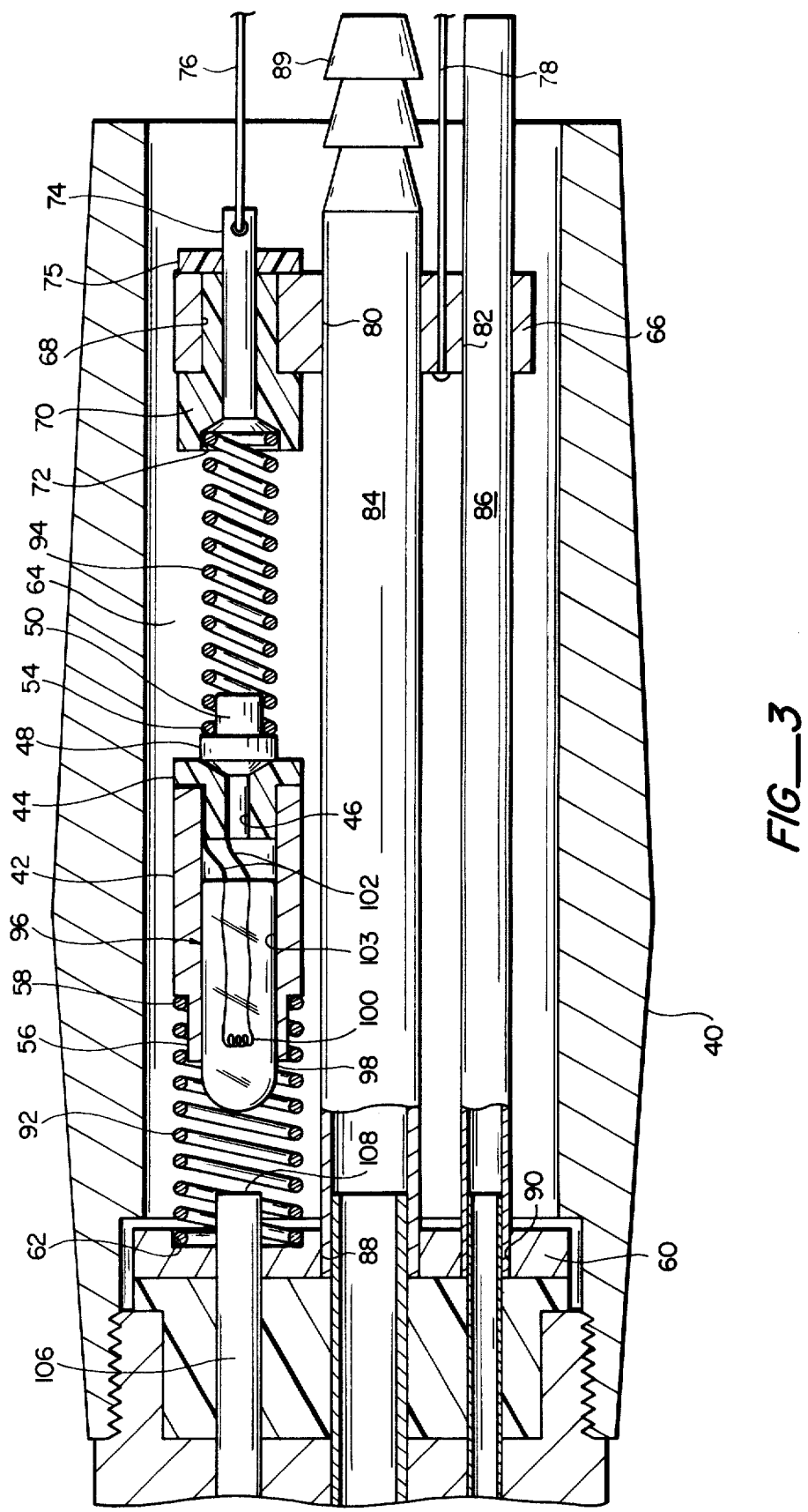
FIG_3

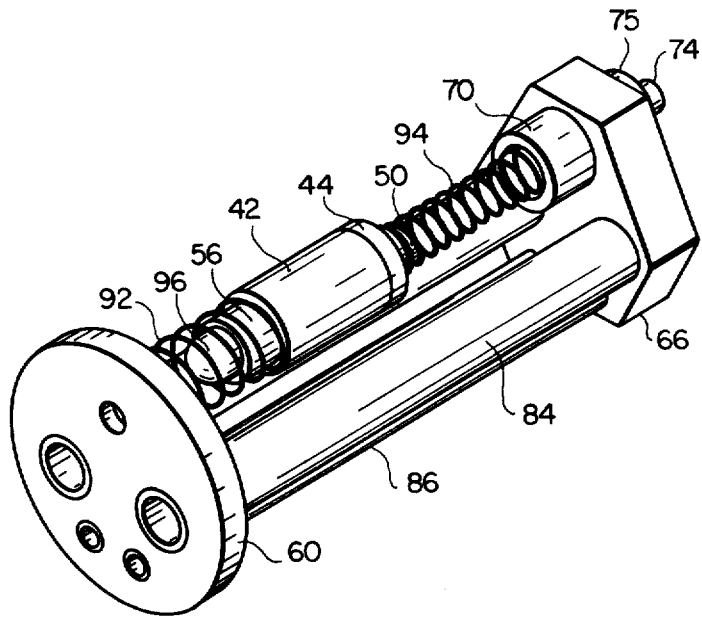
FIG_4
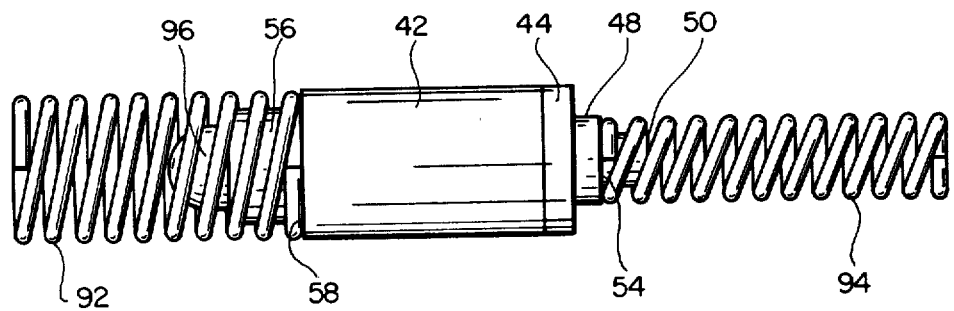
FIG_5

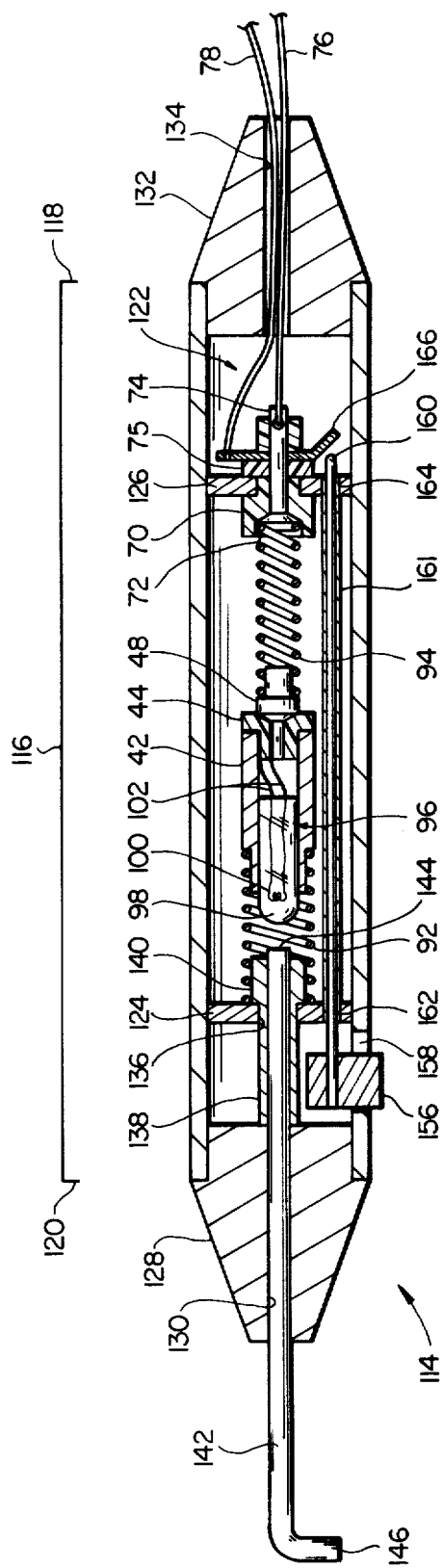
FIG_6
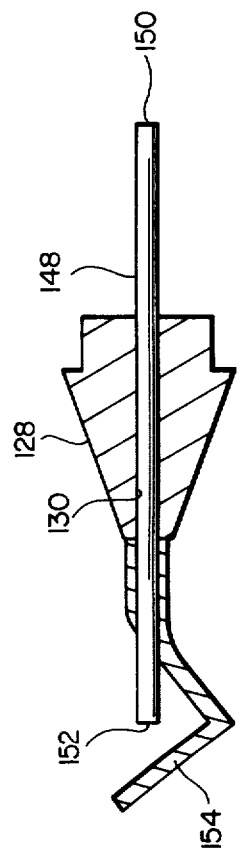
FIG_7

DENTAL INSTRUMENT HAVING A LAMP ASSEMBLY SUSPENSION INCLUDING VIBRATION AND THERMAL ISOLATION MEANS

This is a continuation of application Ser. No. 012,630, filed Feb. 16, 1979 now abandoned.

BACKGROUND OF THE INVENTION

1. Field

Dental instruments equipped with light sources are well-known. Of particular interest herein are dental handpieces and other instruments of a type in which a heat-producing, vibration-sensitive light source is isolated from other portions of the dental instrument.

2. State of the Art

Illumination of a region surrounding the working end of a dental instrument by means of a light source attached directly to the instrument is of significant advantage over the older arrangement of a remotely positioned high-intensity lamp used in combination with a hand-held mirror. In U.S. Pat. No. 3,614,414 to Gores there is described a dental handpiece having a light source within a casing attached to an exterior, rearward end portion of the handpiece. Light is transmitted from the rearward end to the forward or working end of the handpiece by light-guiding means comprising a pair of fiber optic bundles attached along the outside of the handpiece. A disadvantage of a light source and light guide attached to the outside of a dental instrument arises from improper instrument balance so that good tactile control may be difficult to maintain. Also, positioning of the light source along the exterior of the instrument increases the likelihood of contact of a hot portion of the light source casing with the instrument user or with the delicate tissues of a patient's face or mouth.

One attempt at solving the problem of heat generated by a light source mounted on a gas-driven dental handpiece is described in U.S. Pat. No. 3,634,938 to Hutchinson wherein both the compressed air for driving the motor and a stream of water for cooling the operating area are used to cool the light source. This is accomplished by providing a bulky assembly of a cooling coil around the lamp and an air chamber around the lamp and cooling coil through which compressed air passes. The bulky assembly may, however, constitute an impairment to proper tactile control of the instrument by the user. Moreover, cooling a lamp with compressed air may be detrimental to certain types of lamps, especially tungsten-halogen type lamps which must operate at high temperatures for proper efficiency.

A problem especially peculiar to dental handpieces having rotatably driven cutting tools is the vibration generated by the rotating tool and its driving mechanism, such as a high-speed gas-driven motor which typically drives a rotating tool at speeds of 250,000 to 450,000 r.p.m. The vibration transmitted through the handpiece to a bulb mounted on the handpiece may shorten the working life of the lamp filament. Moreover, as a high-speed gas-driven motor attains working speed, there typically occurs a "critical frequency" or a speed of rotation of the motor shaft-and-work tool combination which is at or near the natural frequency of vibration of the lamp filament. Resonant vibration of a lamp filament with the gas-driven motor at the lamp filament critical frequency may quickly destroy a lamp filament. Also, filament-destroying vibrations may be generated during ordinary use of the handpiece when a user forces a rotating bur against a tooth during a cutting or grinding operation, which slows the rotation of the bur and creates "chatter".

There is need, therefore, for a dental instrument having a handle-mounted light source wherein the instrument is thermally isolated from the light source and wherein the light source lamp filament is substantially isolated from vibration generated by a handpiece gas-driven motor or by routine manipulation of the dental instrument.

SUMMARY OF THE INVENTION

A dental instrument equipped with a light source, which instrument is characterized by means providing for reductions in transfer of heat or vibration between the light source and other portions of the dental handpiece, may be provided by housing or casing means, light guiding means having a first terminus within the housing or casing means and a second terminus outside of the housing means, light source mounting means within the housing means for holding a light source in close proximity to the first terminus of the light guiding means, the mounting means having a pair of electrical contacts for making electrical connection to power source connecting means, and support means within the housing or casing means for supporting the light source mounting means, the support means comprising resilient means having properties of resilience, low mass relative to the mass of the mounting means and low thermal conductivity so that transfer of heat and/or mechanical vibration between the housing or casing means and the light source mounting means through the support means is substantially inhibited during use of the dental instrument. Typically, a dental instrument of this invention may have support means comprising first resilient means and second resilient means attached in opposed spaced relationship between the light source mounting means and the housing or casing means.

In an alternative embodiment, a dental instrument can have connected at its proximal end a detachable light source adapter comprising first rigid support means, second rigid support means spaced apart and rigidly connected with the first rigid support means, light source mounting means suspended between the first and second rigid support means, first resilient suspension means connected between the first rigid support means and the light source mounting means, second resilient suspension means connected between the second rigid support means and the light source mounting means, the first and second resilient suspension means having properties of resilience and low mass relative to the mass of the mounting means so that transfer of heat and/or mechanical vibration between the rigid support means and the light source mounting means through the suspension means is substantially inhibited during use of a dental instrument equipped with the light source mounting adapter.

In either of a dental handpiece having a light source built into the handpiece housing or of a detachable light source adapter, each of the first and second resilient support means may comprise a compression-type coil spring. Generally, the light source may be provided by a filament-type lamp operably mounted in the light source mounting means. A dental instrument of this invention may be further characterized by the light source, the light source mounting means and the two compression springs forming a lamp suspension assembly which has properties of mass, thermal capacity and resilience within specified bounds to provide substantial reduction in the transfer of vibration of heat conduction between the housing or casing means and the assembly.

Typically, each of the coil springs is interposed in a pre-loaded condition between the light source mounting means and portions of the housing or casing means. The housing or casing means may further include first socket means for supportably receiving one end of the first coil spring and second socket means for supportably receiving one end of the second coil spring, the first and second sockets affixed to the housing or casing means in facing relationship to each other. The light source mounting means comprises an electrically conductive, elongated sleeve having an axis which intersects each of the first and second socket means. The sleeve has an electrically non-conductive plug frictionally engaged within one end of the sleeve, the sleeve having at its other end an annular-shaped boss portion extending in an axial direction. Also, the plug has an electrically conductive boss portion isolated from the sleeve which boss portion projects in an axial direction. The first and second coil springs may be fabricated of an electrically conductive material and thus may serve as the power conducting means to the lamp assembly from power connecting means located on the housing or casing means. The first coil spring has one end engaged with the plug boss portion and its other end positioned within the first socket means. The second coil spring has one end engaged with the sleeve boss portion and its other end positioned within the second socket means. Power connecting means may be positioned within each of the first and second socket means to make electrical contact with the coil springs.

The lamp assembly and its suspension may typically have mass and resilience properties describable by comparison to a conventional mass-spring harmonic oscillator system. The system includes a mass, m, comprising the lamp and the lamp mounting means; the mass of the spring is neglected inasmuch as it is relatively small in comparison to the total mass of the lamp assembly and its suspension. Although the lamp assembly and its suspension typically comprise two coil springs, the harmonic system in its simplest case will be described as including one coil spring having a spring force constant, k. The purpose of the coil spring is to attenuate the amplitude of the vibration as generated, for example, by a gas-driven motor, which vibration is transmitted from a handpiece housing or casing to the lamp assembly. The differential equation for a simple harmonic oscillator system for vibratory displacement, x, of mass, m, connected to a spring having a force constant, k, with respect to time, t, as related to the vibratory displacement, y, of the handpiece, may be stated as:

$$m \frac{d^2x}{dt^2} = k(y - x) \quad \text{(I)}$$

The amplitude of vibratory displacement, y, of the handpiece housing, where phase differences in the relative motions of the handle housing and lamp assembly are neglected, may be defined by the equation $$y = A \sin \omega t \quad \text{(II)}$$

wherein A is the peak amplitude of housing vibration, $\omega$ is the angular driving frequency of the handpiece motor turbine, and t is the time within which the displacement takes place. One solution to equation I may be stated as $$x = r^2 A \sin \omega t \quad \text{(III)}$$

wherein $r = (W_n/\omega)$, where $W_n$ = is the natural frequency of vibration of the lamp assembly as defined by $\sqrt{k/m}$.

Generally, it is desirable that the lamp assembly mass, m, and the spring force constant, k, be chosen such that the lamp assembly natural vibration frequency, $W_n$, is much less than the gas-driven motor angular frequency, $\omega$. Typically, $W_n$ may be as low as about 300 Hz while $\omega$ may be as high as 7000 Hz, with substitution of these values in the relationship $r = W_n/\omega$ giving a vibration attenuation ratio, $r^2$, of 0.0018.

The light source for the lamp assembly may comprise a filament-type lamp operably mounted in the light source mounting means. A filament lamp found particularly useful is a tungsten halogen type lamp which operates most efficiently when the temperature of the glass envelope of the lamp exceeds 250° C. Lamp life is generally inversely related to the length of warm-up time or the amount of time that the lamp operates at a temperature below its most efficient operating range, or both. If the lamp support or mounting conducts heat away from the lamp to an appreciable extent so as to delay lamp warm-up, or if the temperature of the lamp is lowered by loss of heat from the lamp by contact with exhaust air from the gas-driven motor or by conduction through the lamp mounting and support means, the life of the lamp filament may be considerably shortened.

Thermal losses by conduction of heat from the lamp through the compression springs to the instrument housing may be related to the temperature rise of the lamp envelope as expressed by the differential equation:

$$MC \frac{dT}{dt} = \frac{dQ_{elec}}{dt} - \frac{dQ_R}{dt} - \frac{dQ_C}{dt} - \frac{dQ_k}{dt} \quad \text{(IV)}$$

wherein
- M = mass of the assembly;
- C = heat capacity of the assembly;
- (dT/dt) = instantaneous rate of temperature change of the assembly with respect to time;
- ($dQ_{elec}$/dt) = rate of heat produced by the light source;
- ($dQ_R$/dt) = rate of heat lost by radiation from the light source
- ($dQ_k$/dt) = rate of heat lost by conduction from the light source through the coil springs;
- ($dQ_C$/dt) = rate of heat lost by conduction from the light source to the atmosphere surrounding the light source.

One advantage provided by the lamp assembly suspension of this invention is attributable to the low value of the quantity of heat, ($dQ_k$/dt, rate of lost by conduction from the light source through the coil springs.

A dental instrument of the invention may usually include work tool connecting means on one end of the instrument, such as an adjustable tool-gripping collet. Connected to the work tool connecting means may be any one of many types of dental work tools such as a mirror, an explorer, a probe, a scaler, an excavator, a plugger, a file, a reamer, pliers, a spatula, a restoration tool, forceps, a spreader, a condenser, or any of the various well-known types of burrs or drilling or polishing tools.

The dental instrument may include means for providing work-producing motion to the work tool connecting means, such as a gas-driven motor, although electrically driven motors may be used as well. The motor may include an adjustable collet for gripping a work tool, the motor being disposed with respect to a terminus of the light guiding means so that light emitted from the terminus illuminates a region about a work tool when the work tool is operably engaged by the collet.

DESCRIPTION OF PREFERRED EMBODIMENTS

The means providing the features and advantages of the present invention are illustrated in the accompanying drawings wherein:

FIG. 1 is a side elevational view of a dental handpiece which may suitably include the lamp mounting assembly and suspension of this invention;

FIG. 2 is a partial sectional view of the dental handpiece of FIG. 1 showing placement of the lamp mounting assembly with respect to other components of the handpiece;

FIG. 3 is an enlarged sectional view of the lamp mounting assembly and support means of FIG. 2;

FIG. 4 is a perspective view of the lamp mounting assembly and support means shown separately from the handpiece housing;

FIG. 5 is a side elevational view of the lamp mounting assembly of this invention removed from the handpiece housing;

FIG. 6 is a side elevational view in section of a dental probe having the lamp mounting assembly of this invention; and FIG. 7 is a side elevational view of one attachment suitable for use with the light probe of FIG. 6.

Illustrated in FIG. 1 is a dental handpiece 10 having a handle portion 12 which includes a proximal end 14 and a distal end 16. At distal end 16 of handle portion 12 is a neck 18 to which is attached a head portion 20. In FIG. 2 there is shown in partial cross-section various components of the dental handpiece. Contained as a part of head portion 20 is a high-speed gas-driven motor which includes a motor housing 22 having therein a turbine cartridge assembly 24. Turbine cartridge assembly 24 includes a rotor shaft 26 journalled on a pair of ball-bearing type roller bearing assemblies 28 (shown in block form) disposed on opposite sides of a rotor 30 which is fixedly secured to rotor shaft 26. A plurality of vanes 32 fixedly secured to rotor 30 impart rotation to rotor shaft 26 when a high speed jet of air (or other gas) impinges upon rotor vanes 32, as is well known in the art. A more detailed description of a high speed gas-driven motor that includes a turbine cartridge assembly particularly suitable for the dental handpiece of this invention is found in U.S. application Ser. No. 947,215, filed Sept. 29, 1978 of F. W. Kerfoot, Jr.

Also illustrated with the dental handpiece of FIGS. 1 and 2 is a shank 34 of a work tool that is clasped by an adjustable collet 36 threadedly engaged within a longitudinal bore 38 of rotor shaft 26. Additional details and advantages of construction of a dental handpiece having the illustrated collet may be found in U.S. Pat. No. 3,120,706 to Turchi et al, the disclosure of which is incorporated herein by reference. A description of means for inserting and removing a work tool, such as a dental bur, into and from collet 36 may be found in U.S. Pat. No. 3,947,966 to Lieb et al.

As shown in FIG. 2, there is provided at proximal end 14 of handle portion 12 a housing or casing 40 for light source mounting means 41 depicted in block form. The light source mounting means comprises a lamp assembly, its resilient suspension and first and second rigid support means attached to housing 40. As shown in more detail in FIG. 3, the lamp assembly comprises an elongated sleeve 42 having an axis generally parallel with the longitudinal axis of handle portion 12. At one end of sleeve 42 is an electrically non-conductive plug 44 having an axially disposed bore 46 within which there is engaged an electrically conductive pin 48 providing a cylindrically shaped boss portion 50 projecting in the axial direction away from sleeve 42, which boss portion 50 includes an annular-shaped shoulder 54. Projecting from the other end of sleeve 42 is an annular-shaped sleeve extension 56 having a diameter less than that of sleeve 42. Sleeve extension 56 projects in an axial direction away from sleeve 46 and thus defines an annular-shaped shoulder 58.

The rigid support means comprises a support plate 60 rigidly connected to handpiece 10 at one end of housing 40. A socket 62 is formed as an annular shaped depression within a wall portion of plate 60 facing into chamber 64 of housing 40. In opposed and spaced relationship with support plate 60 is another support plate 66 fabricated of an electrically conductive material. Passing through support plate 66 is a hole 68 within which is affixed a flanged bushing 70 fabricated of an electrically non-conductive material. Within a wall portion of bushing 70 which faces into chamber 64 of housing 40 is a socket 72 formed as an annular-shaped depression. Frictionally fitted within socket 72 and passing through bushing 70 is an electrically conductive contact pin 74 which is secured to support 66 by an insulating washer 75. Attached to one end of contact pin 74 is a service wire 76 which provides connection to one side of an electrical power source (not shown). A second service wire 78 is connected at one end to the other side of the power source (not shown) and at its other end to an electrically conductive portion of support plate 66.

As shown in FIG. 3, rigid support plate 66 has holes 80 and 82 passing therethrough. Air and water supply tubes 84 and 86 pass through holes 80 and 82, respectively, and then into holes 88 and 90, respectively, of support plate 60. Air supply tube 84 is frictionally engaged with or soldered to the walls of holes 80 and 88 in support plates 66 and 60, respectively, and has sufficient rigidity to secure support plate 66 in a rigid position with respect to housing 40 and support plate 60. Air supply tube 84 is fabricated of an electrically conductive material and thus provides a conductive path connecting second service wire 78 to electrically conductive support plate 60.

Inasmuch as support plate 66 is attached securely to rigid plate 60 by means of the described engagement with air supply tube 84, there is no requirement for contact of support plate 66 to housing 40. Hence, there is less contact of the lamp assembly with housing 40 and consequently a reduction in transfer of heat and vibration between the same. Moreover, the single support plate 60 provides an easily removable unit, as shown in FIGS. 4 and 5, which thereby increases the ease of installation and removal of the lamp mounting assembly from a dental instrument for replacement of the bulb.

External connections to sources of compressed air and water are made by air hose 85 and water hose 87, respectively. Air hose 85 is connected to air supply tube 84 at a flanged end 89. Air tube 84 provides a flow of air for imparting rotation to turbine cartridge assembly 24, as described above. Water supply tube 86 provides water to spray forming discharge ports 91 located outside of neck 18 and adjacent head portion 20. The water spray cools a dental bur during a drilling operation. Other suitable spray forming means, together with details of construction, may be found in U.S. Pat. No. 3,525,154 to N. H. Lieb.

The suspension for the lamp assembly, as shown in more detail in FIGS. 3–5, comprises first and second resilient connecting means connected between the light source mounting means and portions of the housing means. The first resilient means is provided by first coil spring 92 which is interposed in a compressed condition between sleeve 42 and rigid support plate 60, with one end of coil spring 92 seated within socket 62 and the other end engaged around sleeve extension 56. Similarly the second resilient means is provided by a second coil spring 94 which is interposed in a compressed condition between sleeve 42 and rigid support plate 66, with one end of coil spring 94 seated within socket 72 and the other end engaged about cylindrical boss 50.

The lamp mounting assembly typically provides mechanical support and electrical connections for a filament-type bulb or lamp 96 having a glass envelope 98 enclosing a resistance wire filament 100 connected across a pair of leads 102. Mechanical support for lamp 96 is provided by sleeve engagement between an inner wall 103 of sleeve 42 with glass envelope 98. One of leads 102 is clasped between adjacent wall portions of electrically conductive sleeve 42 and non-conductive plug 44. The other of leads 102 is clasped between adjacent wall portions of non-conductive plug 44 and electrically conductive pin 48. A power delivering circuit is thus provided by first service wire 76 connected to an electrically isolated contact pin 74 which passes through bushing 70 into the base of socket 72 which, in turn, is in contact with second coil spring 94 fabricated of an electrically conductive material. Engagement of coil spring 94 with boss portion 50 provides electrical connection to one of the pair of leads 102 by way of electrically conducting pin 48. One end of conductive sleeve 42 is in contact with the other of lamp leads 102 while its other end is in electrical contact with first coil spring 92 which is fabricated of conductive material, spring 92 being seated within socket 62. Electrical connection to second service wire 78 is completed through air supply tube 84 engaged with first and second conductive plates 60 and 66, respectively.

Control of electric power to the lamp may be provided by an externally located switch, such as a foot control switch (not shown) which may also control the delivery of air to the gas-driven motor. A suitable foot control switch is described in U.S. Pat. No. 3,596,102 to G. W. Brooks. Also suitable as a power control switch is a delay switch for maintaining power to the light for a short period of time after air flow is interrupted to the gas driven motor, such as the switch circuit disclosed in U.S. application Ser. No. 863,289 filed Dec. 22, 1977 in the name of John E. Nash, the disclosure of which is incorporated herein by reference. Another suitable switch is disclosed in combination with a dental light probe having the lamp mounting means of the invention, as depicted in FIG. 6 herein, which may be adapted to a handpiece as well as a light probe or other dental instrument.

Generally, a power source could be provided by a dry cell battery of 12 volts or less, or a similar low-voltage could be supplied from a transformer mounted on a dental console connected to a 120 v A.C. source.

Practically any type of high intensity lamp may be used as the light source. One preferred light source is a tungsten-halogen type filament lamp having a filament operating voltage requirement of about 4.5 volts. It is generally required, in order to achieve peak operating efficiency and long filament life, that the glass envelope of a tungsten-halogen lamp quickly reach and be maintained at an operating temperature of at least 250° C. The factors affecting the rate of lamp glass envelope warm-up have been set forth above in discussion of equation IV. Generally, improvements and advantages provided by reduction in transient heat loss from the lamp assembly are attributable to the resilient suspension means of the invention. For example, it is preferred that each of coil springs 92 and 94 have characteristics of low thermal conductivity. Hence, in order to minimize loss of heat through the lamp assembly suspension, it is preferred that coil springs 92 and 94 have a long path length as provided by a large number of coils and be fabricated of a wire having a minimum cross-sectional area compatible with providing a minimum degree of radial rigidity so as to prevent contact of the lamp assembly with the walls of housing 40. For example, a spring wire can have a cross-sectional area of 0.0003 square inch, as compared to a typical lamp mounting conducting area of 0.12 square inch, and the spring can have a heat conducting length of 4.5 inches as compared to the 0.25 inch conductive path of a typical lamp mounting. Each of these factors, conductor cross-section and length, affect how long it may take for a lamp to warm-up inasmuch as the greater the transient heat loss by conduction through the mounting the longer it takes for the lamp to reach operating temperature. Also, the described sleeve-plug-coil spring lamp assembly has a lower total mass as compared to conventional lamp assemblies. Hence, a light source mounted in the lamp assembly of the invention, will reach operating temperature more quickly and will retain more heat between light-emitting cycles than when secured in conventional light source mountings. These features are especially advantageous in dental applications where there may be many repeated cycles of lamp use, the cycles often being of one minute duration or less.

The described lamp assembly suspension also provides for attenuation or damping of vibration generated by a gas-driven motor or by routine manipulation of the instrument, which vibration may be transmitted from housing 40 to the lamp assembly. Mathematical expressions describing the desired degree of vibration attenuation were developed in equations I to III. A wide variety of springs may be selected which satisfy the criteria set forth in these equations. Generally, for most handpiece or dental instrument requirements it is desired that coil springs be chosen which have a free length in the range of 0.10 inch to 1.0 inch, with approximately 10 to 20 coils per inch, and which have a coil diameter in the range of 0.100 inch to 0.300 inch. Suitable wire cross-sectional areas may range from $5 \times 10^{-5}$ square inch to $80 \times 10^{-5}$ square inch. Suitable materials from which the coil springs may be fabricated include beryllium copper, silver, aluminum, brass, phosphor bronze and tin-plated steel. Coil springs selected within the ranges of the aforementioned criteria should also have sufficient electrical conductivity to provide suitable links in the power delivering circuit and also should provide adequate thermal isolation within the criteria set forth in equation IV. Where coil springs are used having low electrical conductivity, additional wire conductors could be used to make electrical connection between sleeve 42 and socket 62 and between boss portion 50 and contact pin 74.

One type of light guiding means which may be used in combination with the light source mounting means of the invention is depicted in the handpiece of FIGS. 2 and 3. The light guiding means is provided by a fiber optic bundle 106 having a first terminus 108 projecting into housing 40 from the base of socket 62. It is preferred that first terminus 108 be in proximate axial alignment with lamp 96 and be closely adjacent to the end of lamps 96 so that a maximum amount of light enters first terminus 108 of the light guiding means. A second terminus 110 is positioned outside of the handle portion 12 so as to direct light into the region of a work tool, such as a dental bur 112 operably engaged by collet 36. Light guiding means could be provided by structures other than a fiber optic bundle. For example, a lens or a tube such as a "light pipe" having an interior wall of reflective material may be used to focus or direct light for a short distance from a light source to a region of illumination.

The light source mounting means and assembly may be utilized in other dental instruments as well. For example, as shown in FIG. 6 a light probe 114 comprises a handle portion 116 having a proximal end 118 and a distal end 120. A portion of the interior of handle portion 116 provides a housing or casing 122 for a light source mounting suspended between a forward rigid support plate 124 and a rearward rigid support plate 126. Sleevably fitted within handle portion 116 at distal end 120 is a bushing 128 having an axial bore 130 therethrough. Similarly, sleevably fitted within proximal end 118 of handle portion 116 is a bushing 132 having an axial bore 134.

The lamp assembly within housing 122 is similar to that described in FIGS. 3-5 so that reference may be made to elements having like numerals for detailed description thereof.

Within a bore 136 passing through rigid support 124 is a sleeve 138 having an inner diameter substantially the same as the diameter of bore 130 of bushing 128. Sleeve 138 is in alignment with bore 130 and extends through support plate 124 so as to form a cylindrically-shaped boss portion 140 projecting into housing 122. The forward end of coil spring 92 is engaged about boss portion 140 while the rearward end of coil spring 94 is engaged within socket 72. The lamp assembly resilient suspension for the dental probe of FIG. 6 has the aforementioned advantages of vibration damping and thermal isolation where the resilient suspension comprises coil springs having certain physical characteristics as set forth above in discussion of the handpiece of FIGS. 3-5.

Light guiding means for the dental probe of FIG. 6 is provided by a light pipe 142 which may be typically a fiber optic bundle passing through bore 130 and sleeve 138. Light pipe 142 has a first terminus 144 disposed closely adjacent lamp 96 and a second terminus 146 outside of the probe. An alternative attachment for dental probe 114 is shown in FIG. 7. Bushing 128 has within axial bore 130 a light pipe 148 having a first terminus 150 that may be positioned adjacent lamp 96 when bushing 128 is fitted to probe 114. A second terminus 152 is positioned adjacent a V-shaped mirror 154 affixed to the forward end bushing 128.

The power delivery circuit for the light probe of FIG. 6 is similar to that of the circuit of the dental handpiece of FIGS. 3-5, except that probe 114 may be fitted with a manually operable switch. The switch comprises a tab 156 extending through a slot 158 in a forward section of handle portion 116. Tab 156 is rigidly affixed to a plunger rod 160 which extends through guide tube 161 mounted in guide holes 162 and 164, respectively, of rigid support plates 124 and 126. A flexible contact element 166 secured to insulating bushing 70 provides a stop for plunger rod 160 and thereby completes a circuit for delivery of power to lamp 96.

While this invention has been described with reference to specific embodiments thereof, it should be understood by those skilled in this art that various changes may be made and equivalents may be substituted without departing from the true spirit and scope of this invention. All such modifications are intended to be within the scope of the claims appended hereto.

What is claimed is:

1. A dental instrument for providing intraoral illumination comprising:
   (a) housing means;
   (b) light guiding means having a first terminus associated with said housing means and a second terminus outside of said housing means;
   (c) light source mounting means within said housing means for holding a light source in close proximity to said first terminus of said light guiding means and free from contact with said housing means, said mounting means constituting the sole support of said light source and having a pair of electrical contacts for making electrical connection to power source connecting means; and
   (d) support means within said housing means for supporting said light source mounting means, said support means comprising resilient means constituting the sole suspension of said light source mounting means therefrom and said resilient means having properties of resilience and low mass relative to the mass of said mounting means so that transfer of heat and/or mechanical vibration between said housing means and said light source mounting means through said resilient means is substantially inhibited during use of said dental instrument.

2. The dental instrument of claim 1 further including work tool connecting means on one end of said instrument.

3. The dental instrument of claim 2 further including a work tool operably connected to said work tool connecting means, said work tool selected from the group consisting of a mirror, an explorer, a probe, a scaler, an excavator, a plugger, a file, a reamer, pliers, a spatula, a restoration tool, forceps, a spreader, a condenser, a dental burr, a drilling tool and a polishing tool.

4. The dental instrument of claim 2 wherein said work tool connecting means comprises an adjustable collet for gripping a work tool.

5. The dental instrument of claim 2 further including means for providing work-producing motion to said work tool connecting means.

6. The dental instrument of claim 5 wherein said means for providing work-producing motion is a gas-driven motor.

7. The dental instrument of claim 1 wherein said light guiding means comprises one or more fibers capable of transmitting light.

8. The dental instrument of claim 1 wherein said support means comprises first and second resilient means disposed in substantially opposed spaced relationship between said light source mounting means and opposed portions of said housing in contact therewith.

9. The dental instrument of claim 8 wherein each of said first and said second resilient support means comprises a coil spring.

10. The dental instrument of claim 9 further including a light source comprising a filament-type lamp operably mounted in said light source mounting means.

11. The dental instrument of claim 10 wherein said light source, said light source mounting means and said coil springs comprise an assembly, said assembly having properties of mass and thermal capacity within the bounds approximately defined by the following expression:

$$MC \frac{dT}{dt} = \frac{dQ_{elec}}{dt} - \frac{dQ_R}{dt} - \frac{dQ_C}{dt} - \frac{dQ_k}{dt}$$

wherein
M = mass of said assembly;
C = heat capacity of said assembly;
$(dT/dt)$ = instantaneous rate of temperature change of said assembly;
$(dQ_{elec}/dt)$ = rate of heat produced by said light source;
$(dQ_R/dt)$ = rate of heat lost by radiation from said light source;
$(dQ_k/dt)$ = rate of heat lost by conduction from light source through said coil springs;
$(dQ_C/dt)$ = rate of heat lost by convection from said light source to the atmosphere surrounding said light source.

12. A dental handpiece comprising:
a handle portion having a proximal end and a distal end;
a head portion connected to said handle portion distal end, said head portion including a gas-driven motor capable of rotatably driving a work tool;
casing means associated with said handle portion;
light source support means within said casing means, said light source support means comprising light source mounting means constituting the sole support of a light source for maintaining said light source free from contact with said casing means, first resilient connecting means and second resilient connecting means, each of said first and second resilient connecting means connected between said light source mounting means and portions of said casing means and constituting the sole suspension of said light source mounting means;
means for electrically connecting said light source support means to electric power source connecting means; and
light guiding means having a first terminus adjacent said light source support means and having a second terminus adjacent said distal end to direct light from a light source to the vicinity of a work tool, when said light source support means includes an operating light source and said gas-driven motor has operably associated therewith a work tool.

13. The dental handpiece of claim 12 further including an adjustable collet for gripping a work tool, said collet operably associated with said gas-driven motor.

14. The dental handpiece of claim 12 wherein said first resilient connecting means comprises a first coil spring and said second resilient means comprises a second coil spring, each of said coil springs interposed in a pre-loaded condition between said light source mounting means and portions of said casing means.

15. The dental handpiece of claim 14 wherein
said casing means further includes first socket means for supportably receiving one end of said first coil spring and second socket means for supportably receiving one end of said second coil spring, said first and second sockets affixed to said casing means in facing relationship to each other;
said light source mounting means comprises an electrically conductive, elongated sleeve having an axis which intersects each of said first and second socket means, said sleeve having an electrically non-conductive plug frictionally engaged within one end of said sleeve, said sleeve having at its other end an annular-shaped boss portion extending in an axial direction, said plug including an electrically conductive boss portion isolated from said sleeve, said boss portion projecting in an axial direction;
each of said first and second coil springs is fabricated of an electrically conductive material;
wherein said first coil spring has one end engaged with said plug boss portion and has its other end positioned within said first socket means and wherein said second coil spring has one end engaged with said sleeve boss portion and its other end positioned within said second socket means.

16. The dental instrument of claim 14 further including a light source operably mounted in said light source mounting means.

17. In a dental instrument having the capability of providing intraoral illumination, wherein the instrument includes housing means having light source mounting means, connecting means providing both mechanical support for said light source mounting means within said housing means and electrical connection of said light source mounting means to electric power source connecting means, light guide means having a first terminus adjacent said light source mounting means and having a second terminus outside of said housing means for delivering light from a light source mountable within said light source mounting means to illuminate a region outside of said housing means, the improvement comprising:
said connecting means comprising electrically conductive first resilient means connected between said light source mounting means and said housing means and electrically conductive second resilient means connected between said light source mounting means and said housing means, said light source mounting means maintaining said light source free from contact with said housing means and constituting the sole support of said light source, said first and second resilient means connected to spaced-apart portions of said light source mounting means and constituting the sole suspension of said light source mounting means therefrom, each of said electrically conductive first and second resilient means having a property of resilience, low thermal conductivity and a low mass relative to the mass of said light source mounting means sufficient to substantially inhibit the transfer by conduction through said connecting means of mechanical vibration or of heat, or both, between said light source mounting means and said housing means.

18. The dental instrument of claim 17 wherein each of said first and second resilient means comprises a coil spring.

19. The dental instrument of claim 18 wherein said housing means further includes first socket means for supportably receiving one end of said first coil spring and second socket means for supportably receiving one end of said second coil spring, said first and second socket means affixed to said housing means in facing relationship to each other;

said light source mounting means comprises an electrically conductive, elongated sleeve having an axis which intersects each of said first and second socket means, said sleeve having an electrically non-conductive plug frictionally engaged within one end of said sleeve, said sleeve having at its other end an annular-shaped boss portion extending in an axial direction, said plug including an electrically conductive boss portion isolated from said sleeve, said boss portion projecting in an axial direction;

each of said first and second coil springs is fabricated of an electrically conductive material;

wherein said first coil spring has one end engaged with said plug boss portion and has its other end positioned within said first socket means and wherein said second coil spring has one end engaged with said annular-shaped sleeve boss portion and its other end positioned within said second socket means.

20. The dental instrument of claim 17 further including a light source mounted in said light source mounting means.

21. The dental instrument of claim 20 wherein said light source is a filament lamp.

22. The dental instrument of claim 21 wherein said filament lamp is a tungsten-halogen type lamp.

23. The dental instrument of claim 17 further comprising a work tool operably connected to said instrument adjacent said second terminus of said light guiding means.

24. The dental instrument of claim 17 further including an end portion having a gas-driven motor, said gas-driven motor having an adjustable collet for gripping a work tool, said gas-driven motor disposed with respect to said second terminus of said light guiding means so that light emitted from said second terminus illuminates a region about a work tool when the work tool is operably engaged by said collet.

25. A dental handpiece comprising:

a housing means;

work tool connecting means within said housing means;

driving means associated with said work tool connecting means for providing work-producing motion to said work tool connecting means;

light guiding means having a first terminus within said housing means and a second terminus outside of said housing means;

light source mounting means within said housing means for holding a light source in close proximity to said first terminus of said light guiding means and free from contact with said housing means, said mounting means constituting the sole support of said light source and having a pair of electrical contacts for making electrical connection to power source connecting means; and support means within said housing means for supporting said light source mounting means, said support means comprising resilient means constituting the sole suspension of said light source mounting means therefrom and said resilient means having properties of resilience and low mass relative to the mass of said mounting means so that transfer of heat and/or mechanical vibration between said housing means and said light source mounting means through said resilient means is substantially inhibited during use of said dental handpiece.

26. The dental handpiece of claim 25 wherein said work tool connecting means comprises an adjustable collet for gripping a work tool.

27. The dental handpiece of claim 25 wherein said driving means is a gas-driven motor.

28. The dental handpiece of claim 25 wherein said support means comprises first resilient connecting means and second resilient connecting means, each of said first and second resilient connecting means connected between said light source mounting means and portions of said housing means.

29. The dental handpiece of claim 28 wherein said first resilient connecting means comprises a first coil spring and said second resilient means comprises a second coil spring, each of said coil springs interposed in a pre-loaded condition between said light source mounting means and portions of said housing means.

30. The dental handpiece of claim 29 wherein said housing means further includes first socket means for supportably receiving one end of said first coil spring and second socket means for supportably receiving one end of said second coil spring, said first and second sockets affixed to said housing means in facing relationship to each other;

said light source mounting means comprises an electrically conductive, elongated sleeve having an axis which intersects each of said first and second socket means, said sleeve having an electrically non-conductive plug frictionally engaged within one end of said sleeve, said sleeve having at its other end an annular-shaped boss portion extending in an axial direction, said plug including an electrically conductive boss portion isolated from said sleeve, said boss portion projecting in an axial direction;

each of said first and second coil springs being fabricated of an electrically conductive material;

wherein said first coil spring has one end engaged with said plug boss portion and has its other end positioned within said first socket means and wherein said second coil spring has one end engaged with said sleeve boss portion and its other end positioned within said second socket means.

31. The dental instrument of claim 25 further including a light source operably mounted in said light source mounting means.

32. The dental handpiece of claim 29 wherein said light source, said light source mounting means and one of said coil springs comprise an assembly, said assembly having a mass, m, and said coil spring having a spring force constant, k, so that the natural frequency of vibration of the assembly, $W_n$, wherein $W_n = <k/m$, provides a vibration attenuation ratio, $r^2$, less than about 0.1, wherein $r^2 = [W_n/\omega]^2$, with $\omega$ equal to the angular frequency of the gas-driven motor.

33. A light source adapter for a dental instrument, said adapter comprising:
   first rigid support means;
   second rigid support means spaced apart and rigidly connected with said first rigid support means;
   light source mounting means suspended between said first and second rigid support means for maintaining a light source free from contact with said first and second rigid support means, said light source mounting means constituting the sole support of said light source;
   first resilient suspension means connected between said first rigid support means and said light source mounting means;
   second resilient suspension means connected between said second rigid support means and said light source mounting means;
   said first and second resilient suspension means constituting the sole suspension of said light source mounting means and having properties of resilience and low mass relative to the mass of said mounting means so that transfer of heat and/or mechanical vibration between said rigid support means and said light source mounting means through said suspension means is substantially inhibited during use of said dental instrument.

34. The light source adapter of claim 33 wherein said first resilient suspension means comprises a first coil spring and said second resilient suspension means comprises a second coil spring, each of said coil springs interposed in a pre-loaded condition between said light source mounting means and portions of said first and second rigid support means.

35. The light source adapter of claim 34 wherein said first rigid support means further includes first socket means for supportably receiving one end of said first coil spring and said second rigid support means further includes second socket means for supportably receiving one end of said second coil spring, said first and second sockets affixed to said first and second rigid support means means in facing relationship to each other;
   said light source mounting means comprises an electrically conductive, elongated sleeve having an axis which intersects each of said first and second socket means, said sleeve having an electrically non-conductive plug frictionally engaged within one end of said sleeve, said sleeve having at its other end an annular-shaped boss portion extending in an axial direction, said plug including an electrically conductive boss portion isolated from said sleeve, said boss portion projecting in an axial direction;
   each of said first and second coil springs is fabricated of an electrically conductive material;
   wherein said first coil spring has one end engaged with said plug boss portion and has its other end positioned within said first socket means and wherein said second coil spring has one end engaged with said sleeve boss portion and its other end positioned within said second socket means.

36. The light source adapter of claim 33 further including a light source operably mounted in said light source mounting means.

37. The light source adapter of claim 33 wherein said first rigid support means includes connecting means for attaching said light source adapter to a handpiece housing, said second rigid support means being supported by said first rigid support means out of contact with the handpiece housing.

* * * * *